United States Patent [19]
Josic et al.

[11] Patent Number: 5,919,909
[45] Date of Patent: Jul. 6, 1999

[54] PROCESS FOR THE PREPARATION OF FACTOR IX FROM BIOLOGICAL SOURCES

[75] Inventors: Djuro Josic, Vienna; Lutz Hoffer, Baden, both of Austria; Frank Morfeld, Eschborn, Germany

[73] Assignee: Octapharma AG, Ziegelbrucke, Switzerland

[21] Appl. No.: 08/894,654

[22] PCT Filed: Feb. 14, 1996

[86] PCT No.: PCT/EP96/00636

§ 371 Date: Nov. 26, 1997

§ 102(e) Date: Nov. 26, 1997

[87] PCT Pub. No.: WO96/27003

PCT Pub. Date: Sep. 6, 1996

[30] Foreign Application Priority Data

Feb. 25, 1995 [DE] Germany .................. 195 06 633

[51] Int. Cl.$^6$ .................. A61K 35/14; C12N 7/04
[52] U.S. Cl. .................. 530/384; 530/381; 530/382; 530/383; 530/412; 530/413; 530/414; 530/416; 530/418; 530/422; 530/427; 435/236; 435/238; 435/239; 424/529; 424/532
[58] Field of Search .................. 530/384, 381, 530/382, 383, 412, 413, 414, 416, 418, 422, 427; 435/236, 238, 239; 424/529, 532

[56] References Cited

U.S. PATENT DOCUMENTS

| 4,687,664 | 8/1987 | Philopitsch et al. | 424/85 |
| 5,281,661 | 1/1994 | Linnau et al. | 525/541 |
| 5,457,181 | 10/1995 | Michalski et al. | 530/381 |

FOREIGN PATENT DOCUMENTS

92/15324  9/1992  WIPO.

OTHER PUBLICATIONS

"HiLoad™ Phenyl Sepharose® High Performance," Data File, Pharmacia Biotech. (18–1022–55).

Stampe et al., *Journal of Chromatography*, vol. 363, pp. 101–103, 1986.

R. K. Scopes, *Protein Purification: Principles and Practice* (Second Edition), 1987.

Primary Examiner—Cecilia J. Tsang
Assistant Examiner—Abdel A. Mohamed
Attorney, Agent, or Firm—Jacobson, Price, Holman & Stern, PLLC

[57] ABSTRACT

A process for the preparation of factor IX from a biological source by chromatography involves prior treatment with ammonium sulfate as a protein precipitant at a concentration of from 1.5–2.3 mol/l.

13 Claims, 1 Drawing Sheet

F IX Process

```
                                                              spec. act.

Starting material:    plasma/cryopoor plasma                  ≈ 0.01
                              ↓
                       - fibrinogen ↓
                       - F VIII ↓

Capture:    DEAE ion exchange solid phase extraction or chromatography   0.5-1

- Ig ↓
                       - albumin ↓ vitamin K dependent coagulation factors: 10-50 IU/ml
            enrichment factor for F IX: ≈ 3500

Further purification:    ammonium sulfate precipitation       1-5
                              1.75-1.9 mol/l

- proteins C/S ↓ depletion F II: ≈ 80%
            depletion F VII: ≈ 100%

Elimination of prot. activity:   HIC tentacle chromatography   5-15 depletion of proteolytic activity: 100%
            depletion F VII: 100%

Polishing:         heparin affinity chromatography            100-200 depletion F II: 100%
            depletion F X: 100%

F IX final concentration: 50 IU/ml
            enrichment factor for F IX: ≈ 8000
```

F IX Process spec. act.

Starting material: plasma/cryopoor plasma ≈ 0.01
↓
- fibrinogen ↓
- F VIII ↓

Capture: DEAE ion exchange solid phase extraction or chromatography   0.5-1

- Ig ↓
- albumin ↓ vitamin K dependent coagulation factors: 10-50 IU/ml
enrichment factor for F IX: ≈ 3500

Further purification: ammonium sulfate precipitation   1-5
1.75-1.9 mol/l

- proteins C/S ↓ depletion F II: ≈ 80%
depletion F VII: ≈ 100%

Elimination of prot. activity: HIC tentacle chromatography   5-15 depletion of proteolytic activity: 100%
depletion F VII: 100%

Polishing: heparin affinity chromatography   100-200 depletion F II: 100%
depletion F X: 100%

F IX final concentration: 50 IU/ml
enrichment factor for F IX: ≈ 8000

PROCESS FOR THE PREPARATION OF FACTOR IX FROM BIOLOGICAL SOURCES

SUMMARY OF THE INVENTION

The present invention pertains to a process for the preparation of factor IX from biological sources by chromatography as well as to factor IX obtainable by the process according to the invention.

When factor IX is prepared, for example, from blood plasma, the cryoprecipitate is first separated. The frozen citrate plasma is thawed and the major amount of factor VIII and fibrinogen is separated by centrifugation. The cryopoor plasma thus obtained contains the vitamin K dependent coagulation factors with an activity in the order of magnitude of 0.01 IU/mg of protein.

According to the process known from the prior art, the vitamin K dependent coagulation factors are bound by extraction with anion exchangers, such as DEAE Sephadex, without adversely affecting albumin recovery. However, due to the poor flow characteristics of DEAE Sephadex, this step must usually be performed as a solid phase extraction in batch operation. The fractions obtained after elution of the DEAE Sephadex then serve as the starting material for the purification of factor IX. Proteases contained in the plasma, however, are also enriched in this fraction, resulting in yield losses of the material of interest, factor IX, by proteolytic digestion and an increase of the risk of thrombogenity of the preparation.

The object of the invention is to provide a process which reduces the risks mentioned without the addition of protease inhibitors.

Surprisingly, this object is achieved by a process with the features of the claim. This involves treating the biological source containing factor IX with a protein precipitant. Candidate biological sources are, in particular, blood plasma or cryoprecipitate depleted of factor VIII and fibrinogen (cryopoor plasma).

The concentration of the protein precipitant is, in particular, from 1.5 to 2.3 mol/l, preferably from 1.75 to 1.9 mol/l. The values relate to the protein precipitant concentrations present in the sources containing factor IX (final concentration).

As the protein precipitant, ammonium sulfate is considered in particular.

BRIEF DESCRIPTION OF THE DRAWING

FIG. 1 is a flow chart illustrating chromatographic purification according to the instant invention.

The process according to the invention reduces the proteolytic activity by at least one order of magnitude. In addition, interfering components, such as factor VII and factor II, are removed by the precipitation step prior to the actual chromatographic purification of factor IX. Proteins C and S are also depleted. In the case of factor VII, almost complete elimination can be achieved. Factor II is also depleted rather completely (70 to 90%) whereas depletion of proteins C and S is about 50%.

In the supernatant of the fraction treated with the protein precipitant, the activity of factor IX is typically from 20 to 30 IU/ml, corresponding to a specific activity of 1 to 5 IU/mg.

The precipitation step according to the invention, preferably using ammonium sulfate, is followed by the chromatographic separation of the fraction enriched in factor IX. This takes advantage of the fact that at high salt concentrations proteins can undergo hydrophobic interactions to different extents. According to the invention, factor IX is preferably bound in the presence of relatively high salt concentrations, which are present from protein precipitation, to a chromatographic material capable of being employed for hydrophobic interaction chromatography (HIC). This at the same time reduces the high salt concentration resulting from protein precipitation. In particular, a chromatographic material may be used which has bound on the substrate material a hydrophilic flexible arm (tentacle). Covalently bound to these spacers are then the corresponding ligands, in particular hydrophobic ligands, such as propyl, butyl, phenyl groups.

The supernatant of the fraction treated with the protein precipitant is applied to the appropriate chromatographic material and optionally washed. Elution of the factor IX bound to the column and still containing factor X can be performed with a buffer containing the protein precipitant in a lower concentration, the ionic strength of the eluent solution thus being reduced with respect to that of the application solution. The fraction comprising factor IX eluting from the chromatographic column which contains HIC material is collected and subjected to further desalting steps using appropriate means. This can be performed, for instance, by ultrafiltration and/or diafiltration.

Further separation of factor IX, for example, from accompanying factor X, is performed in a preferred embodiment of the present invention by affinity chromatography on a heparin modified substrate. When the ionic strength of the solution containing the factors is relatively low, the latter will bind to the chromatographic material. Elution of interfering factor X, if any, is achieved by treatment with a solution containing sodium chloride in concentrations of from 150 to 300 mmol/l. Under such conditions, factor IX will remain bound to the heparin affinity substrate. Upon increasing the ionic strength of the aqueous solution to about twice its value, factor IX starts separating from the surface of the affinity substrate.

Virus inactivation may be performed by chemical and/or physical processes. The physical virus inactivation method essentially consists in heat treating the respective fraction at 60 to 65° C. for 5 to 30 hours. Such heat treatment can be performed, in particular, following the heparin affinity chromatography. The chemical virus inactivation consists, for example, in a treatment of a fraction containing factor IX with non-ionic surfactants and dialkyl or trialkyl phosphates. In particular, combinations of Tween and tri-n-butyl phosphate (TNBP) may be used. Methods of virus inactivation are described in EP 0131740 or in Horowitz et al., Blood, 79 (1992) 826.

Virus inactivation methods may also be combined, such as described in WO 94/17834. Preferably, chemical virus inactivation is performed after the ultrafiltration/diafiltration following the hydrophobic chromatography.

By applying the process according to the invention, the overall yield of high purity factor IX can be increased to 20 to 30%, based on plasma.

The FIGURE shows the process according to the invention with subsequent chromatographic purification steps in the form of a flow chart. The arrows indicate which fractions are separated off and which remain in the corresponding eluates and supernatants.

The following example will illustrate the invention.

Frozen citrate plasma is thawed and agitated at 0 to 3° C. Factor VIII and fibrinogen are separated by centrifugation. The cryopoor plasma fraction obtained contains vitamin K dependent coagulation factors with a specific activity of about 0.01 IU/mg of protein. The subsequent capture step includes solid phase extraction or chromatography on DEAE ion exchangers, separating IgG and albumin. The vitamin K dependent coagulation factors are present in an activity of from 10 to 50 IU/ml, corresponding to an enrichment factor of about 3500, based on factor IX.

The capture step is now followed by the actual purification. To the fraction resulting from the capture step is added an ammonium sulfate solution to give a final concentration of about 1.9 mol/l. C and S proteins are removed by about 50% whereas factor II is removed by 70 to 90% and factor VII almost quantitatively. The supernatant obtained from the ammonium sulfate precipitation is subjected to hydrophobic interaction chromatography on an appropriately modified tentacle gel. The concentration of ammonium sulfate in the application solution was about 1.75 mol/l. The application buffer also contains phosphate ions. Hydrophobic interaction chromatography will result in residual factor VII and factor IX being bound. Factor X will bind to the material at 70 to 80%. Elution of the factor IX/factor X mixture is performed with a solution of ammonium sulfate containing from 1.2 to 1.4 mol/l. The eluent is free of factor VII and has essentially no proteolytic activity. The specific activity of factor IX in the factor IX/factor X mixture is from 5 to 15 IU/mg of protein.

The ammonium sulfate present in the eluate is removed by ultrafiltration and diafiltration. Virus inactivation with detergents is performed by treatment with about 1% Tween 80/0.3% TNBP.

Then, after separating the detergent, the fraction obtained is subjected to heparin affinity chromatography. Factors X and IX will bind to the heparin gel at low osmolarities. Factor X is obtained by washing with a buffer containing 0.25 mol/l of NaCl. Factor IX will elute upon increasing the sodium chloride concentration to 0.45 mol/l. Thereafter, factor IX is present in the eluate at 30 to 50 IU/ml with a specific activity of >100.

The fraction thus obtained containing factor IX is desalted and lyophilized.

We claim:

1. A process for the preparation of factor IX from a biological source by chromatography, wherein prior to affinity chromatographic separations said biological source is treated with ammonium sulfate as a protein precipitant at a concentration of from 1.5–2.3 mol/l.

2. The process according to claim 1, wherein said biological source is blood plasma or plasma depleted of factor VIII and fibrinogen by separation of the cryoprecipitate (cryopoor plasma).

3. Factor IX obtained by the process according to claim 1.

4. The process according to claim 1, further comprising removal of the protein precipitant and enrichment of factor IX by adsorption of factor IX to a chromatographic material employed for hydrophobic interaction chromatography (HIC) are performed following protein precipitation.

5. The process according to claim 4, wherein said chromatographic material having adsorbed factor IX is treated with an aqueous solution having an ionic strength resulting in separation of factor IX in solution from said HIC material.

6. The process according to claim 5, wherein said solution obtained after separation of factor IX from said HIC material is subjected to a process step which reduces salt concentration of the solution containing factor IX.

7. The process according to claim 6, which is followed by affinity chromatography on a heparin modified substrate material.

8. The process according to claim 1, further comprising virus inactivation.

9. The process according to claim 8, wherein said virus inactivation comprises heat treatment at 60 to 65° C. for 5 to 30 hours.

10. The process according to claim 8, wherein said virus inactivation comprises further treatment of a sample containing factor IX with non-ionic detergents, dialkylated or trialkylated phosphates.

11. The process according to claim 8, wherein virus inactivation is performed, following said affinity chromatography in heparin.

12. The process according to claim 11, wherein said virus inactivation comprises heat treatment at 60 to 65° C. for 5 to 30 hours.

13. The process according to claim 11, wherein said virus inactivation comprises further treatment of a sample containing factor IX with non-ionic detergents, dialkylated or trialkylated phosphates.

* * * * *